(12) United States Patent
Ueno et al.

(10) Patent No.: US 7,491,166 B2
(45) Date of Patent: Feb. 17, 2009

(54) ENDOSCOPE

(75) Inventors: Haruhiko Ueno, Hachioji (JP); Yasuhito Kura, Hachioji (JP); Koji Yamaya, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/852,737

(22) Filed: May 24, 2004

(65) Prior Publication Data
US 2004/0267090 A1    Dec. 30, 2004

(30) Foreign Application Priority Data
May 27, 2003  (JP) .............. 2003-149891
Feb. 24, 2004  (JP) .............. 2004-048221

(51) Int. Cl.
*A61B 1/00*        (2006.01)
(52) U.S. Cl. .............. 600/107; 600/106; 600/118; 600/129; 600/131; 600/146; 600/147
(58) Field of Classification Search ......... 600/104–106, 600/129, 153
See application file for complete search history.

(56) References Cited

U.S. PATENT DOCUMENTS

| | | | |
|---|---|---|---|
| 3,897,775 A | 8/1975 | Furihata | |
| 4,905,666 A | 3/1990 | Fukuda | |
| 6,066,125 A | 5/2000 | Webster, Jr. | |
| 6,146,355 A * | 11/2000 | Biggs | .............. 604/95.01 |
| 6,458,074 B1 * | 10/2002 | Matsui et al. | .............. 600/106 |
| 6,554,794 B1 | 4/2003 | Mueller et al. | |
| 2003/0040657 A1 | 2/2003 | Yamaya et al. | |
| 2003/0109861 A1 * | 6/2003 | Shimada | .............. 606/14 |

FOREIGN PATENT DOCUMENTS

| | | |
|---|---|---|
| JP | 2001-170006 | 6/2001 |
| WO | WO 00/67834 | 11/2000 |

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

An endoscope includes a therapeutic instrument controlling base which is arranged to the distal portion of the inserting portion and controls such that a therapeutic instrument projected from the opening of a channel for inserting the therapeutic instrument at the distal portion of the inserting portion moves in the right and left directions of an observed image obtained by an observing unit, a controlling-base operating unit which is arranged to an operating section continuously arranged to the proximal side portion of the inserting portion and which can be operated in the right and left directions of an operator who grips the operating section, and a controlling-base operating mechanism which controls such that the therapeutic instrument controlling base moves in the right direction of the observed image according to the operation of the controlling-base operating unit in the right direction thereof by the operator who grips the operating section and controls such that the therapeutic instrument controlling base moves in the left direction of the observed image according to the operation of the controlling-base operating unit in the left direction.

18 Claims, 12 Drawing Sheets

ENDOSCOPE

This application claims benefit of Japanese Application No. 2003-149891 filed on May 27, 2003, and No. 2004-48221 filed on Feb. 24, 2004, the contents of which are incorporated by this reference.

BACKGROUND OF THE INVENTION

1. Field of the Invention

The present invention relates to an endoscope comprising a channel for inserting a therapeutic instrument, in which the therapeutic instrument is projected from the distal portion of the channel for inserting the therapeutic instrument and is moved for performing various treatments.

2. Description of the Related Art

Conventionally, a medical endoscope is widely used for various curing treatments which are performed by inserting a long and thin inserting portion in the body cavity so as to observe the organ in the body cavity or by using a therapeutic instrument inserted in an instrument channel as needed.

Further, recently, an endoscope is widely known for an effective operation, in which the endoscope comprises a plurality of channels for inserting the therapeutic instrument, and the affected part in the body cavity is incised with the endoscope by inserting the therapeutic instrument into the channels for inserting the therapeutic instrument.

As one of the above-mentioned endoscopes, Japanese Unexamined Patent Application Publication No. 2001-170006 discloses a technology to change the direction of the therapeutic instrument which is inserted into the channel for inserting the therapeutic instrument and is projected from a channel opening, wherein the endoscope has two channels for inserting the therapeutic instrument and the therapeutic instrument is operated in the rising and falling direction in view of an operator who grips an operating section by operating a rising table arranged to an opening at the distal portion (channel opening) of the channels for inserting the therapeutic instrument according to the operation of an operating ring which rotates around the axis thereof in the direction coaxial to the operating section.

SUMMARY OF THE INVENTION

According to the present invention, an endoscope comprises:

a long and thin inserting portion which is inserted in an object;

observing means which is arranged to the distal portion of the inserting portion;

a therapeutic instrument controlling base which is arranged to the distal portion of the inserting portion, and moves a therapeutic instrument projected from the opening of a channel for inserting the therapeutic instrument at the distal portion of the inserting portion in the right and left directions of an observed image obtained by the observing means;

controlling-base operating means which is arranged to an operating section continuously arranged to the proximal side portion of the inserting portion and which can be operated in the right and left directions of an operator who grips the operating section; and a controlling-base operating mechanism which controls such that the therapeutic instrument controlling base moves in the right direction of the observed image according to the operation of the controlling-base operating means in the right direction thereof by the operator who grips the operating section and controls such that the therapeutic instrument controlling base moves in the left direction of the observed image according to the operation of the controlling-base operating means in the left direction.

DETAILED DESCRIPTION OF THE PREFERRED EMBODIMENTS

Figure 1:
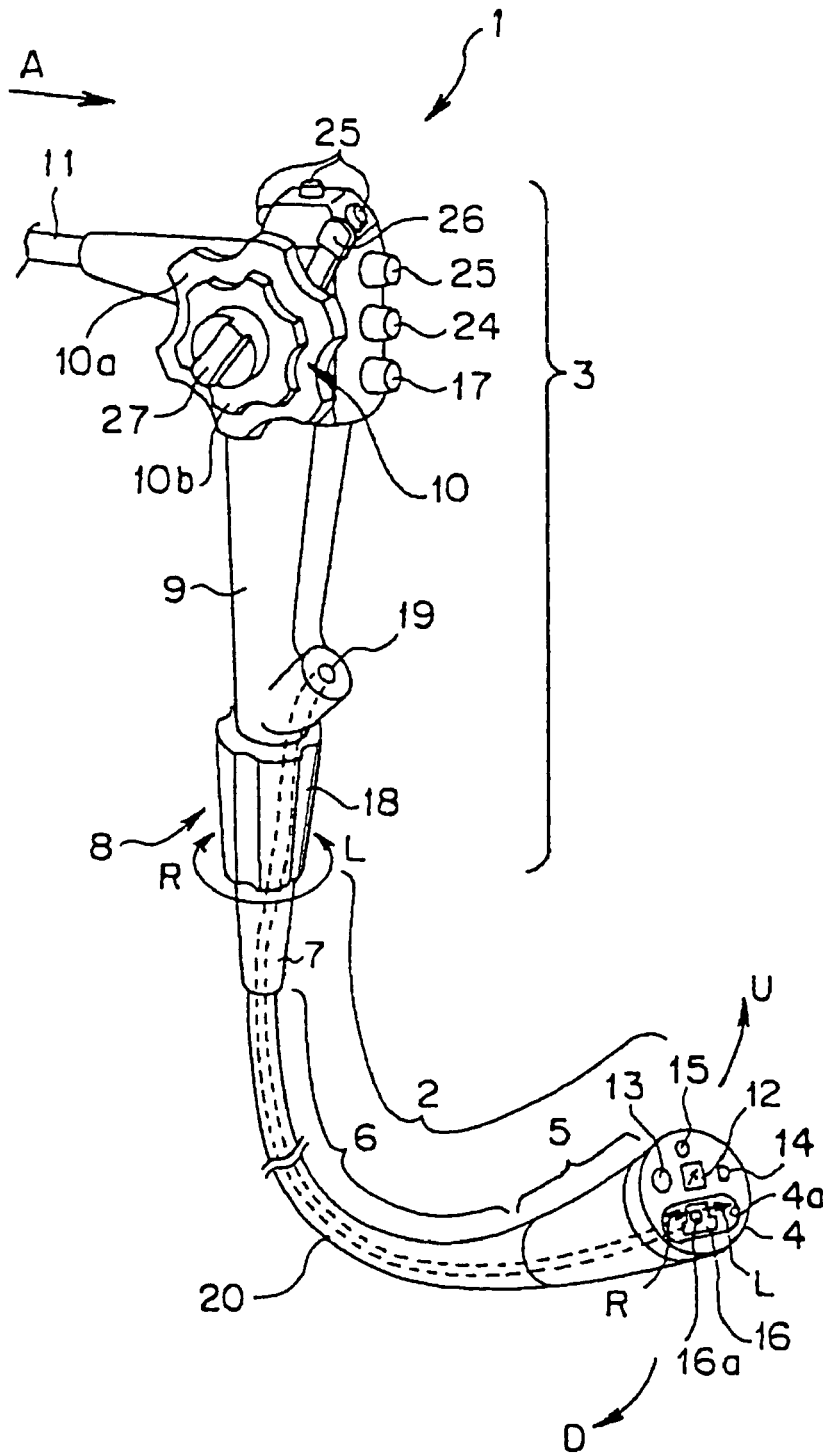
FIG. 1 is a perspective view showing the entire structure of an endoscope according to the first embodiment of the present invention.
Figure 2:
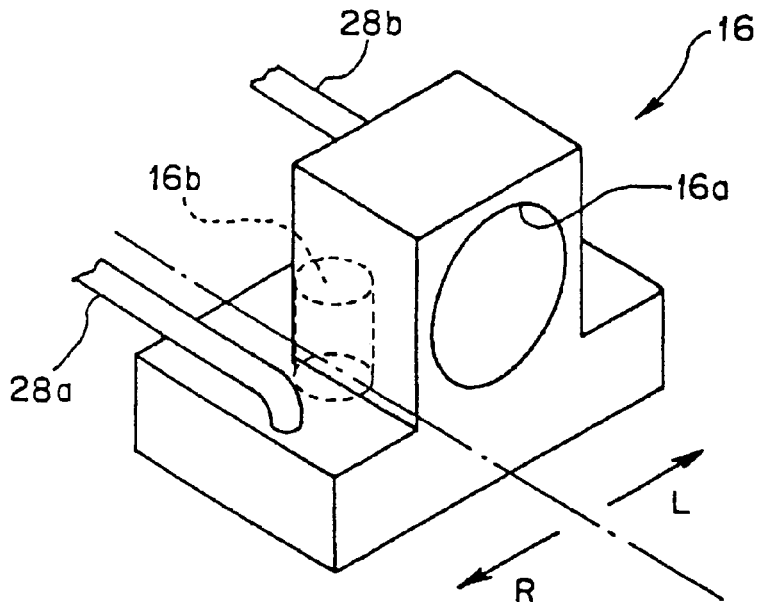
FIG. 2 is a perspective view showing a therapeutic instrument controlling base according to the first embodiment of the present invention.
Figure 3:
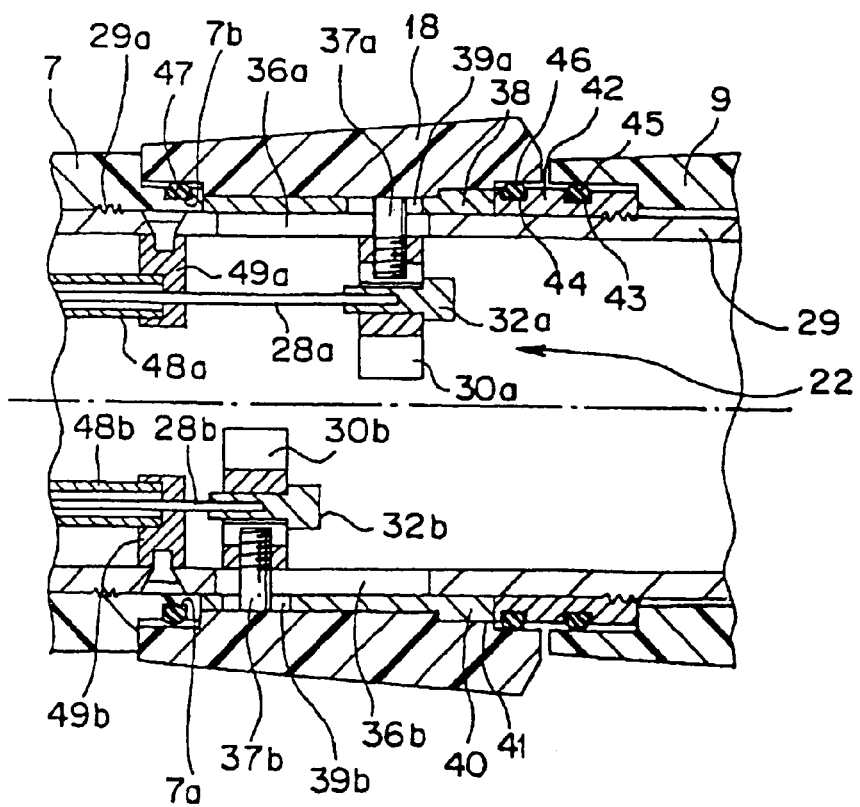
FIG. 3 is a cross-sectional view showing a main portion of a controlling-base operating mechanism according to the first embodiment of the present invention.
Figure 4:
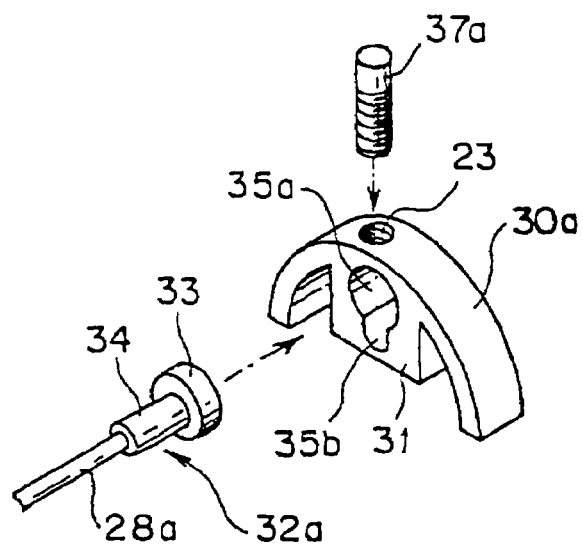
FIG. 4 is an exploded view showing a main portion of a swinging ring and a tractional wire according to the first embodiment of the present invention.
Figure 5:
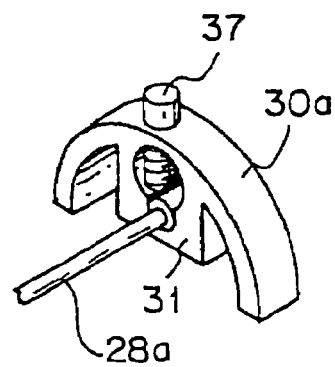
FIG. 5 is a perspective view showing the main portion of the swinging ring and the tractional wire according to the first embodiment of the present invention.
Figure 6:
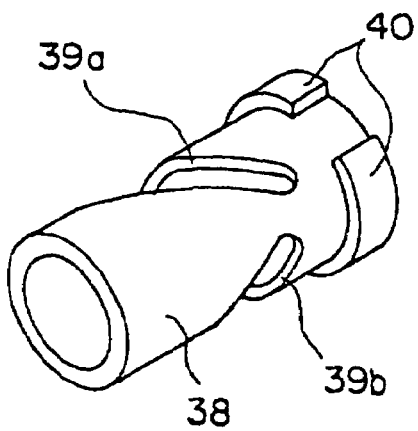
FIG. 6 is a perspective view showing a cam ring according to the first embodiment of the present invention.
Figure 7:
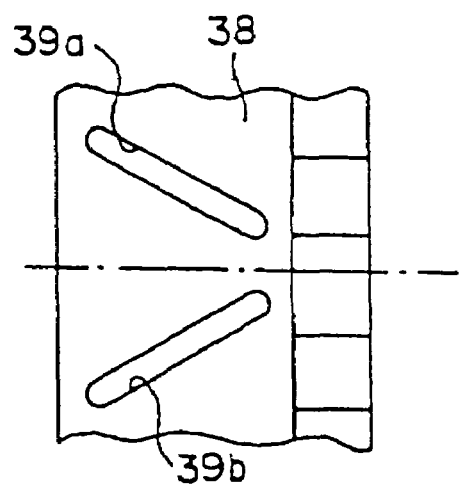
FIG. 7 is a development showing a cam ring according to the first embodiment of the present invention.
Figure 8:
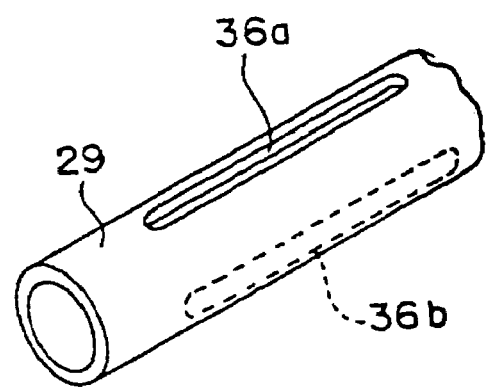
FIG. 8 is a perspective view showing a main portion of an operating section main body according to the first embodiment of the present invention.
Figure 9:
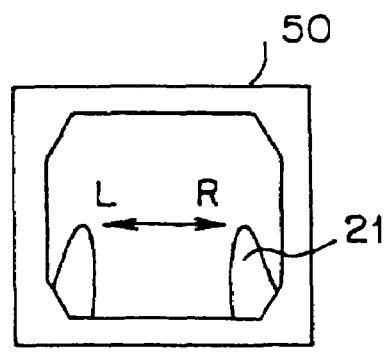
FIG. 9 is an explanatory diagram showing one example of a therapeutic instrument displayed on a monitor screen according to the first embodiment of the present invention.
Figure 10:
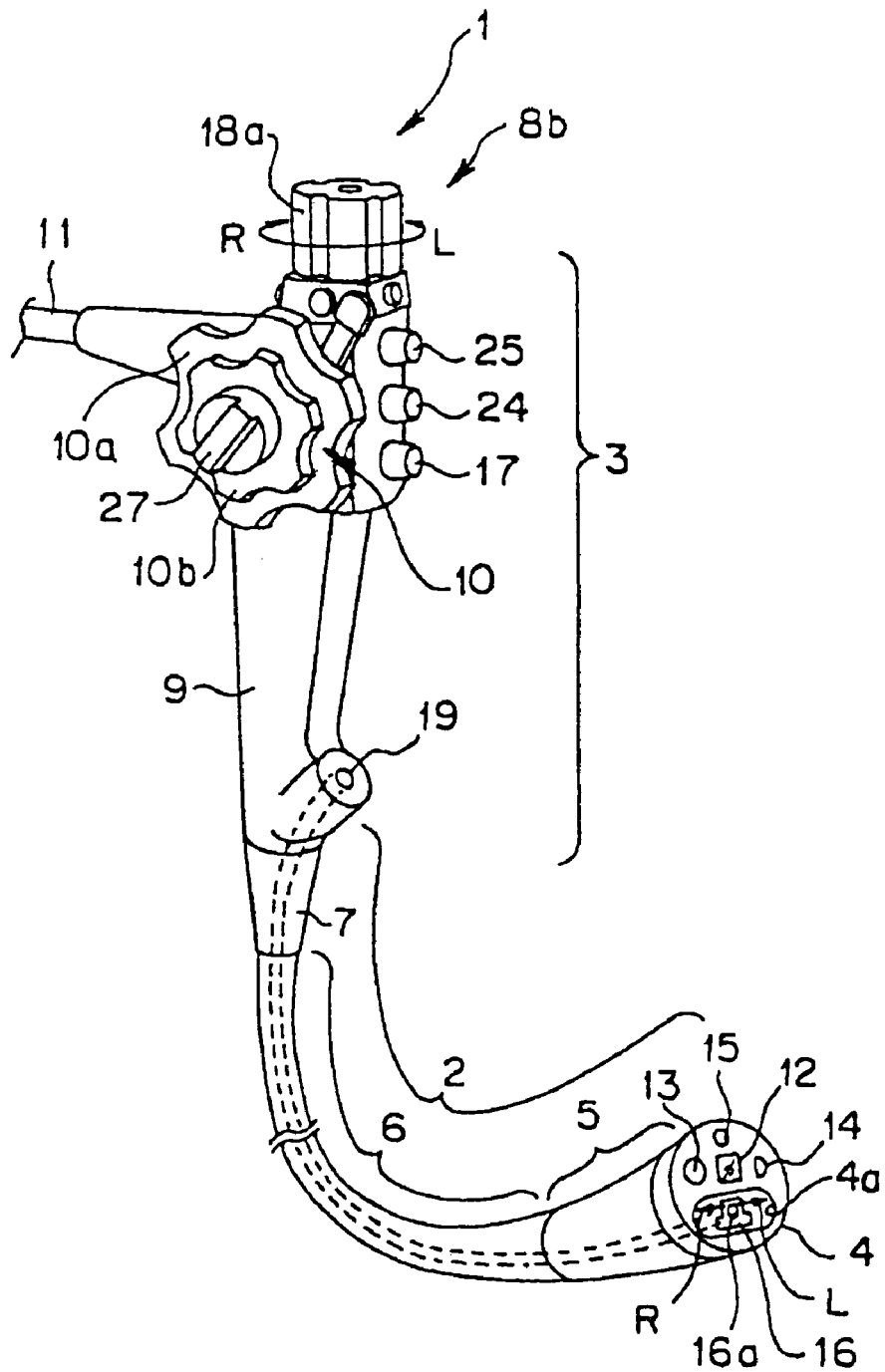
FIG. 10 is a perspective view showing an endoscope according to a modification of the first embodiment of the present invention.

Hereinbelow, a description is given of embodiments with reference to the drawings. FIG. 1 is a perspective view showing the entire structure of an endoscope according to the first embodiment of the present invention. FIG. 2 is a perspective view showing a therapeutic instrument controlling base according to the first embodiment of the present invention. FIG. 3 is a cross-sectional view showing a main portion of a controlling-base operating mechanism according to the first embodiment of the present invention. FIG. 4 is an exploded perspective view showing a main portion of a swinging ring and a tractional wire according to the first embodiment of the present invention. FIG. 5 is a perspective view showing the main portion of the swinging ring and the tractional wire according to the first embodiment of the present invention. FIG. 6 is a perspective view showing a cam ring according to the first embodiment of the present invention. FIG. 7 is a development showing the cam ring according to the first embodiment of the present invention. FIG. 8 is a perspective view showing a main portion of an operating section main body according to the first embodiment of the present invention. FIG. 9 is an explanatory diagram showing one example of a therapeutic instrument displayed on a monitor screen according to the first embodiment of the present invention. FIG. 10 is a perspective view showing an endoscope according to a modification of the first embodiment of the present invention.

First, a description is given of the schematic structure of an endoscope according to the first embodiment. Referring to FIG. 1, reference numeral 1 denotes an endoscope, and the endoscope 1 comprises: a long and thin inserting portion 2; and an operating section 3 which is continuously arranged to the proximal portion of the inserting portion 2.

The inserting portion 2 comprises a main portion which is formed of the distal side thereof, an end section 4, a bending portion 5, a soft flexible (tube) portion 6, and a protection boot portion 7.

The end section of the operating section 3 is connected to the proximal side portion of the protection boot portion 7. The operating section 3 has, from the distal side thereof, a controlling-base operating section 8, a grip-portion casing 9, and a bending operating portion 10. Further, adjacently to the front side of the bending operating portion 10, various control buttons including an air and fluid supply control button 17, a suction control button 24, and an image recording button 25 and the like. Further, a universal cord 11 including a light guide fiber and the like is connected to the operating section 3.

The end section 4 of the inserting portion 2 includes: an observing unit 12 and an illuminating member 13 as observing means for capturing an installed observed image of an object; an air and fluid supply nozzle 14; a front fluid-supply vent 15; and a therapeutic instrument controlling base 16.

The observing unit 12 comprises an objective lens and a solid-state image pick-up element (which are not shown). An image signal of the observed portion, which is formed by the objective lens and is picked-up by the solid-state image pick-up element is transmitted to an image processing device (not shown) by a signal cable wired to the inserting portion 2, the operating section 3, and the universal cord 11. A monitor 50 (refer to FIG. 9) is connected to the image processing device. The image processing device generates a video signal based on the transmitted image signal, and displays the observed image on the monitor 50 based on the generated video signal. In this case, the image processing device records the image signal in accordance with the operation of the image recording button 25 arranged to the operating section 3.

The illuminating member 13 has an illuminating lens (not shown). The illuminating lens irradiates illuminating light guided via the light guide fiber included in the universal cord 11, the operating section 3, and the inserting portion 2 and illuminates the observed portion.

The air and fluid supply nozzle 14 supplies the air and fluid in accordance with the operation of the air and fluid supply control button 17 arranged to the operating section 3.

The front fluid-supply outlet 15 is communicated with a front fluid supply cap (not shown) arranged to a connector (not shown) on the proximal side of the universal cord 11, and the fluid is supplied from a syringe or a fluid supply pump connected to the fluid supply cap.

The therapeutic instrument controlling base 16 is rotatably attached to a concave portion 4a opened to the end section 4. Upon operating a controlling-base operating knob 18 as controlling-base operating means forming the controlling-base operating section 8, the therapeutic instrument controlling base 16 is moved through a pair of tractional wires 28a and 28b as operation communicating members connected to a controlling-base operating mechanism 22 (refer to FIG. 2), which will be described later.

Hereinafter, the operation directions of the portions forming the endoscope 1 are defined as follows.

The directions are defined by setting based on the viewing direction (shown by an arrow A in FIG. 1) of an operator who grips the grip-portion casing 9 (of the operating section 3) in a state in which the inserting portion 2 is vertically positioned and the air and fluid supply control button 17 and the suction control button 24 are arranged forward.

That is, the right directions of the bending, swinging, and rotation of the portions are defined to the right direction (shown by an R direction in FIG. 1) in view of the operator who grips the grip-portion casing 9.

Further, the left directions of the bending, swinging, and rotation of the portions are defined to the left direction (shown by an L direction in FIG. 1) in view of the operator who grips the grip-portion casing 9.

Furthermore, the front directions of the bending and swinging of the portions are defined to the direction matching the direction A, and particularly, the direction (U direction shown in FIG. 1) of the portions in the inserting portion 2 which are bent or swung in the front direction of the protection boot portion 7 is defined to the up direction.

In addition, the rearward directions of the bending and swinging of the portions are defined to the direction opposite to that shown by the arrow A, and particularly, the direction (D direction shown in FIG. 1) of the portions in the inserting portion 2 which are bent or swung in the back direction of the protection boot portion 7 is defined to the down direction.

That is, the right and left bending directions of the bending portion 5 match the right and left directions of the therapeutic instrument controlling base 16.

The up, down, right and left directions of the endoscope image on the monitor 50 and the image of the object observed by the operator are set to the directions matching the above-mentioned up, down, right and left directions.

Referring to FIG. 1, the controlling-base operating knob 18 comprises an operating knob which can be operated in the right and left directions of the operator who grips the grip-portion casing 9. Specifically, the controlling-base operating knob 18 comprises the operating knob which can be rotated in the circumferential direction of the operating section 3, with the long axis of the operating section 3 as the rotating axis (namely, the long axis of the operating section along the distal side from the proximal side of the operating section 3). The therapeutic instrument controlling base 16 moves in the right and left directions in view of the operator who grips the operating section 3 (the grip-portion casing 9). Referring to FIG. 2, the end section of the tractional wire 28a is connected to the right of an axis of movement 16b as the center of the swinging of the therapeutic instrument controlling base 16, and the end section of the tractional wire 28b is connected to the left of the axis of movement 16b.

The end section of a channel 20 for inserting the therapeutic instrument included in the inserting portion 2 is communicated with the proximal side portion of the therapeutic instrument controlling base 16, and a distal end opening 16a opened to the therapeutic instrument controlling base 16 is communicated with the distal end opening of the channel 20 for inserting the therapeutic instrument. The proximal portion of the channel 20 for inserting the therapeutic instrument is extended into the operating section 3, and is further communicated with a therapeutic instrument inserting port 19 opened to the grip-portion casing 9. Thus, the therapeutic instrument (not shown) inserted from the therapeutic instrument inserting port 19 is guided to the therapeutic instrument controlling base 16 via the channel 20 for inserting the therapeutic instrument, and the distal side of the therapeutic instrument is projected from the distal end opening 16a.

The bending portion 5 is formed by making a plurality of bending pieces (not shown) contact with each other, and is bent in the up, down, right and left directions in accordance with the operation of the bending operating portion 10 arranged to the operating section 3. That is, the bending operating portion 10 comprises a knob 10a for operating the bending portion in the up and down directions which bends the bending portion 5 in the up and down directions, and a knob 10b for operating the bending portion in the right and left directions which bends the bending portion 5 in the right and left directions. The knob 10a for operating the bending portion in the up and down directions and the knob 10b for operating the bending portion in the right and left directions are connected to the bending portion 5 via bending wires (not shown). The bending wires advance or return in the operating section 3 and the inserting portion 2 by operating the knob 10a for operating the bending portion in the up and down directions and the knob 10b for operating the bending portion in the right and left directions. Thus, the bending portion 5 is bent in the up, down, right, and left directions. An up-and-down rotation locking lever 26 and a right-and-left rotation locking knob 27 are arranged to the bending operating portion 10, and the rotation of the knob 10a for operating the bending portion in the up and down directions and the knob 10b for operating the bending portion in the right and left directions are appropriately locked in accordance with the operation of the up-and-down rotation locking lever 26 and the right-and-left rotation locking knob 27.

The protection boot portion 7 prevents the bending of the connecting portion between the proximal portion of the flexible (tube) portion 6 and the controlling-base operating section 8. Referring to FIG. 3, the protection boot portion 7 is screwed, via a screw portion 29a, to the outer circumference of the distal side of an operating section main body 29 which is substantially cylindrical-shaped and is arranged in the grip-portion casing 9.

Next, a description is given of the specific structure of the controlling-base operating mechanism 22 which controls the therapeutic instrument controlling base 16.

Referring to FIG. 3, the controlling-base operating mechanism 22 comprises: a cam ring 38 which is rotatably supported to the outer circumference of the operating section main body 29 on the distal side of the grip-portion casing 9; and a pair of sliding members 30a and 30b which can slidably be moved in the longitudinal direction in the operating section main body 29.

Referring to FIGS. 3, 6, and 7, the cam ring 38 comprises a member, to which a plurality of projected portions 40 are projected at the outer circumference on the proximal side and which is substantially cylindrical-shaped. The controlling-base operating knob 18 is arranged to the outer circumference of the cam ring 38. The plurality of projected portions 40 of the cam ring 38 are fit into concave portions formed to the inner circumference of the proximal side of the controlling-base operating knob 18. As a result of the fitting, the cam ring 38 is rotated integrally with the controlling-base operating knob 18.

Referring to FIG. 3, a watertight cylindrical member 42, which is screwed to the outer circumference of the operating section main body 29, is arranged between the cam ring 38 and the grip-portion casing 9. Pair of concave grooves 43 and 44 are arranged to the outer circumference of the watertight cylindrical member 42. Watertight members 45 and 46 such as O-rings are attached to the concave grooves 43 and 44. The watertight member 45 is attached by pressure to the inner circumference of the grip-portion casing 9 on the distal portion thereof, and the watertight member 46 is attached by pressure to the inner circumference of the controlling-base operating knob 18 on the proximal side. As a result of the attachment by pressure, the clearance between the grip-portion casing 9 and the controlling-base operating knob 18 is watertightly sealed. A step portion 7a is formed to the proximal portion of the protection boot portion 7, and a concave groove 7b is circumferentially arranged to the step portion 7a. A watertight member 47 such as an O-ring is attached to the concave groove 7b, and the watertight member 47 is attached by pressure to the inner circumference of the controlling-base operating knob 18 on the distal side thereof. As a result of the attachment by pressure, the clearance between the protection boot portion 7 and the controlling-base operating knob 18 is watertightly sealed.

The cam ring 38 comprises cam grooves 39a and 39b which individually advance and return the sliding members 30a and 30b. The cam grooves 39a and 39b comprise symmetric cam grooves and, according to the first embodiment, referring to FIGS. 6 and 7, the cam groove 39a comprises a cam groove which is clockwisely spiral-shaped from the distal side of the cam ring 38 to the proximal side thereof, and the cam groove 39b comprises a cam groove which is anticlockwisely spiral-shaped from the distal side of the cam ring 38 to the proximal side thereof.

Referring to FIGS. 3 and 5, the sliding members 30a and 30b comprise partly-arcuate members along the inner circumference of the operating section main body 29. Since the sliding members 30a and 30b are similarly shaped, only the sliding member 30a is representatively shown in FIGS. 4 and 5. Referring to FIGS. 4 and 5, thick portions 31 are projected from the inside of the sliding members 30a and 30b, and the thick portion 31 comprises a through-hole 35a with a large diameter and a through-hole 35b with a small diameter, which are pierced in the longitudinal direction. The through-hole 35a and the through-hole 35b are sequentially pierced along the diameter directions of the sliding members 30a and 30b to the outer circumference thereof, and are communicated with each other. Further, a screw hole 23, which is perpendicularly communicated to the through-hole 35a, is pierced to the tops of the sliding member 30a and the sliding member 30b.

Referring to FIGS. 3 and 5, in the sliding members 30a and 30b, the proximal portions of the tractional wires 28a and 28b extended from the therapeutic instrument controlling base 16 side through the inserting portion 2 are connected via connecting caps 32a and 32b.

Specifically, main portions of the connecting caps 32a and 32b are formed by integrating a cylindrical portion 34 with a small diameter, which can be inserted into the through-hole 35b, and a cylindrical portion 33 with a large diameter, which can be inserted into the through-hole 35a. The connecting caps 32a and 32b are fixed to the proximal portions of the tractional wires 28a and 28b by the soldering or brazing. By locking the cylindrical portion 33 into the through-hole 35b, the tractional wires 28a and 28b are connected to the sliding members 30a and 30b. That is, the connecting caps 32a and 32b are inserted into the through-holes 35a that are pierced to the thick portions 31 of the sliding members 30a and 30b. After completely piercing the cylindrical portion 33 through the through-hole 35a, the connecting caps 32a and 32b are moved to the through-hole 35b side and are thus locked. Thereafter, referring to FIG. 5, cam pins 37a and 37b to which male screw portions are formed on the distal side thereof are screwed into the screw holes 23, thereby regulating the movement of the connecting caps 32a and 32b toward the through-hole 35a. Further, the pull-out tendency of the connecting caps 32a and 32b from the sliding members 30a and 30b is prevented.

Here, when cam pins 37a and 37b are screwed into the screw holes 23, the end sections of the cam pins 37a and 37b are projected from the tops of the sliding members 30a and 30b (refer to FIG. 5). Referring to FIG. 3, when the sliding members 30a and 30b are slidably attached to the inner circumference of the operating section main body 29, the cam pins 37a and 37b are pierced through cam pin grooves 36a and 36b (refer to FIGS. 3 and 8) which are pierced through the operating section main body 29 along the longitudinal direction thereof corresponding to the cam grooves 39a and 39b, and are engaged with the cam grooves 39a and 39b. Thus, the operating section 3 comprises the controlling-base operating mechanism 22 which advances and returns the sliding members 30a and 30b according to the rotating operation of the controlling-base operating knob 18.

That is, when the controlling-base operating knob 18 is rotated in the right direction in FIG. 1, the sliding member 30a moves to the proximal side in the operating section main body 29. Further, when the controlling-base operating knob 18 is rotated in the left direction, the sliding member 30a moves to the distal side. On the contrary, when the controlling-base operating knob 18 is rotated in the left direction, the sliding member 30b moves to the distal side in the operating section main body 29 and, when the controlling-base operating knob 18 is rotated in the left direction, it moves to the proximal side in the operating section main body 29.

The tractional wires 28a and 28b are advanced and returned in association with the advance and return operation of the sliding members 30a and 30b. Thus, when the controlling-base operating knob 18 is rotated in the right direction, the therapeutic instrument controlling base 16 is moved in the right direction and, when the controlling-base operating knob 18 is rotated in the left direction, the therapeutic instrument controlling base 16 is moved in the left direction.

Incidentally, referring to FIG. 3, the tractional wires 28a and 28b are extended to the operating section 3 from the inserting portion 2 while they are inserted in operating wire guide tubes 48a and 48b. Guide tube holding members 49a and 49b stand, facing the sliding members 30a and 30b. The proximal portions of the operating wire guide tubes 48a and 48b are fixed to the guide tube holding members 49a and 49b by the soldering or brazing. Consequently, the preferable operability is ensured.

With the structure according to the first embodiment, when the controlling-base operating knob 18 is rotated in the right direction in view of the operator who grips the operating section, the therapeutic instrument controlling base 16 is moved in the right direction. When the controlling-base operating knob 18 is rotated in the left direction, the therapeutic instrument controlling base 16 is moved in the left direction. Thus, the operability improves.

That is, in view of the operator who grips the operating section 3, the operating direction of the controlling-base operating knob 18 matches the swinging direction of the therapeutic instrument controlling base 16 (namely, the swinging direction of the therapeutic instrument 21 on the observed image through the monitor 50) and therefore the operability improves.

Referring to FIG. 9, upon the incision while the operator observes the image of the therapeutic instrument 21 displayed on the monitor 50, the operating direction of the controlling-base operating knob 18 can promptly be determined based on the operating direction of the therapeutic instrument 21 (high-frequency knife and the like) projected from the distal end opening 16a of the therapeutic instrument controlling base 16 via the channel 20 for inserting the therapeutic instrument.

In the conventional endoscope, for example, upon incising the lesion mucous membrane by swinging, e.g., the high-frequency knife in the right and left directions, the lesion mucous membrane is incised by adjusting the height direction (up and down direction) of the high-frequency knife with the angle operation using the up and down operation for the bending, in addition to the swinging operation of the high-frequency knife. In this case, when the controlling-base operating means is adjacently arranged to the bending operating knob, the left hand for operating the bending operating knob interferes with the right hand for operating the controlling-base operating means and, inconveniently, the operation is difficult. However, according to the first embodiment, the controlling-base operating means is arranged near the protection boot portion of the inserting portion (or the up side of the bending operating knob as shown in FIG. 10, which will be described later), namely, is arranged apart from the bending operating knob. Consequently, such a defect is not caused and the high-frequency knife is easily controlled.

According to the first embodiment, referring to FIG. 10, a controlling-base operating knob 18a may be arranged to the proximal portion of the operating section 3, and the controlling-base operating knob 18a may include the same mechanism as that of the controlling-base operating mechanism 22 to form a controlling-base operating section 8a. With the above-mentioned structure, the same advantages are obtained.

Figure 11:
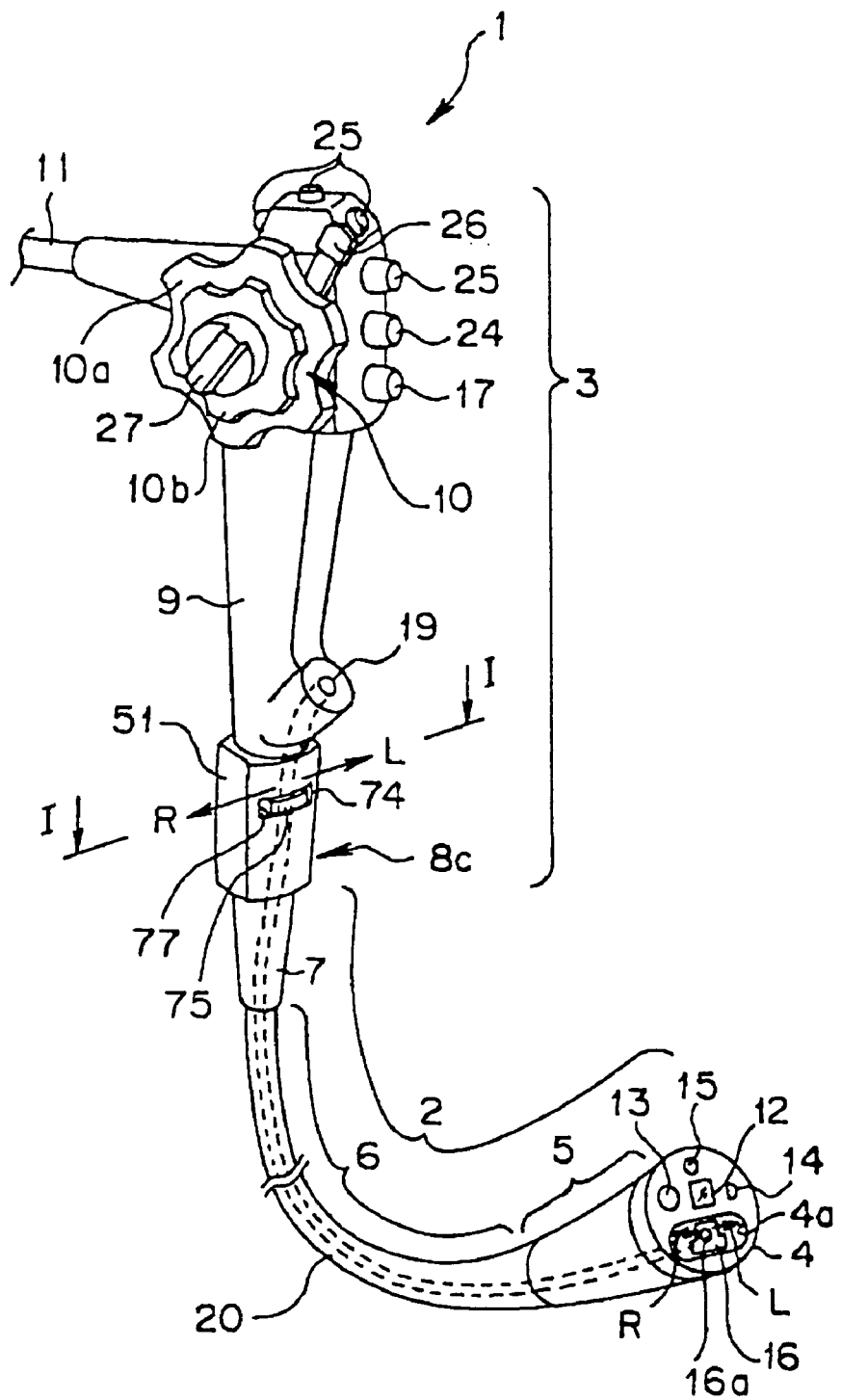
FIG. 11 is a perspective view showing the entire structure of an endoscope according to the second embodiment of the present invention.
Figure 12:
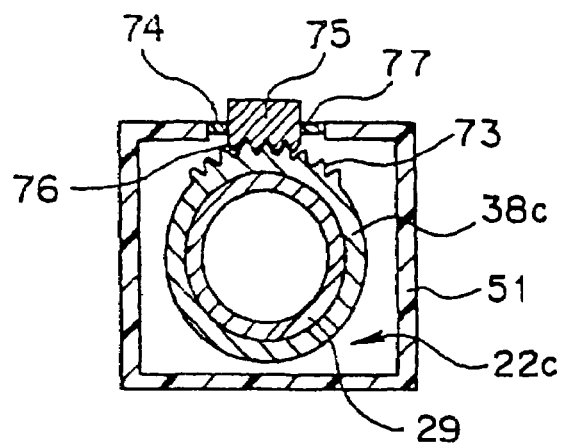
FIG. 12 is a cross-sectional view showing a main portion along the I-I direction in FIG. 11 according to the second embodiment of the present invention.

Next, a description is given of the second embodiment with reference to FIGS. 11 and 12. FIG. 11 is a perspective view showing the entire structure of an endoscope according to the second embodiment of the present invention. FIG. 12 is a cross-sectional view showing a main portion along the I-I direction in FIG. 11 according to the second embodiment of the present invention. According to the second embodiment, unlike the first embodiment, a controlling-base operating section 8c is formed by using a controlling-base operating frame 51 having an operating slider 75, in place of the controlling-base operating knob 18. Others are the same as those of the first embodiment, the same components are designated by the same reference numerals, and a description thereof is omitted.

Referring to FIG. 11, according to the second embodiment, the controlling-base operating frame 51 forming the controlling-base operating section 8c is arranged to the distal side of the operating section 3. A slide groove 74 is thin and long in the right and left directions in view of the operator who grips the operating section 3 and is opened to the controlling-base operating frame 51. The slide groove 74 holds the operating slider 75 as controlling-base operating means which can freely be slid in the right and left directions along the slide groove 74. A watertight member 77 which is sheet-shaped and contains an elastic member is filled between the slide groove 74 and the operating slider 75. The watertight member 77 assures the watertightness between the slide groove 74 and the operating slider 75.

Referring to FIG. 12, the controlling-base operating frame 51 accommodates a controlling-base operating mechanism 22c. The controlling-base operating mechanism 22c has a cam ring 38c which can rotatably be supported to the outer circumference of the operating section main body 29, and a gear 73 arranged to the outer circumference of the cam ring 38c is screwed to a gear 76 arranged to the operating slider 75. The gears 73 and 76 slide the operating slider 75 in the right and left directions and, then, the cam ring 38c is rotated.

Although not shown, similarly to the first embodiment, the operating section main body 29 comprises the pair of the sliding members 30a and 30b which advance and return according to the rotation of the cam ring 38c. The tractional wires 28a and 28b advance and return according to the movement of the sliding members 30a and 30b and thus the therapeutic instrument controlling base 16 is moved in the right and left directions.

That is, when the operating slider 75 is slid in the right direction in view of the operator who grips the operating section 3, the therapeutic instrument controlling base 16 is moved in the right direction. When the operating slider 75 is slid in the left direction, the therapeutic instrument controlling base 16 is moved in the left direction.

According to the second embodiment, the operating direction of the operating slider 75 matches the swinging direction of the therapeutic instrument controlling base 16 and therefore the same advantages as those according to the first embodiment are obtained.

Figure 13:
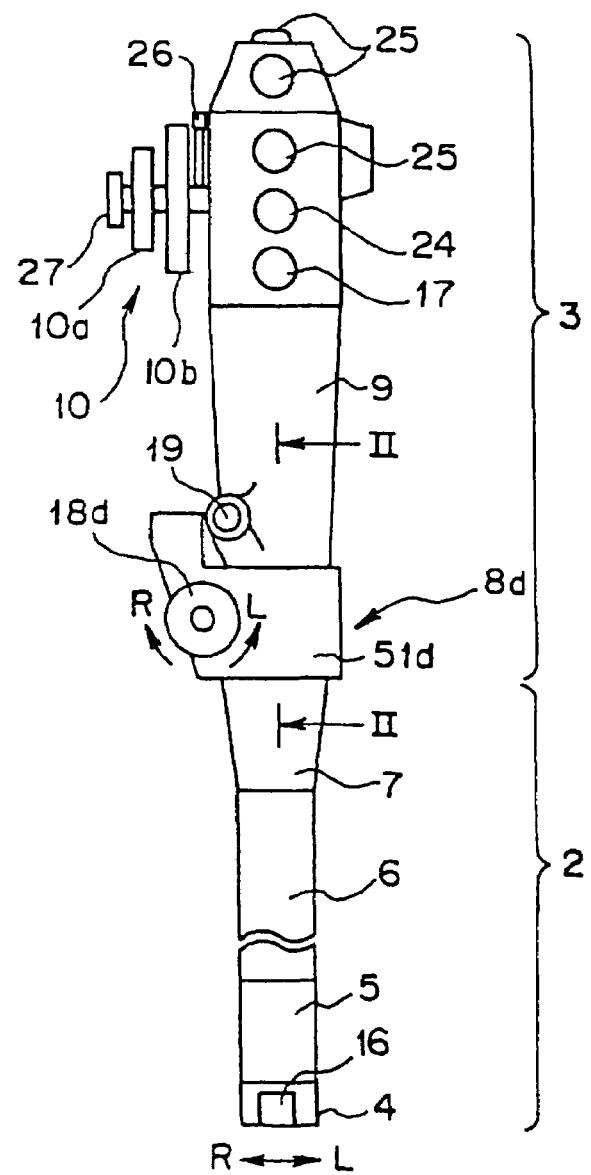
FIG. 13 is a front view showing the entire structure of an endoscope according to the third embodiment of the present invention.
Figure 14:
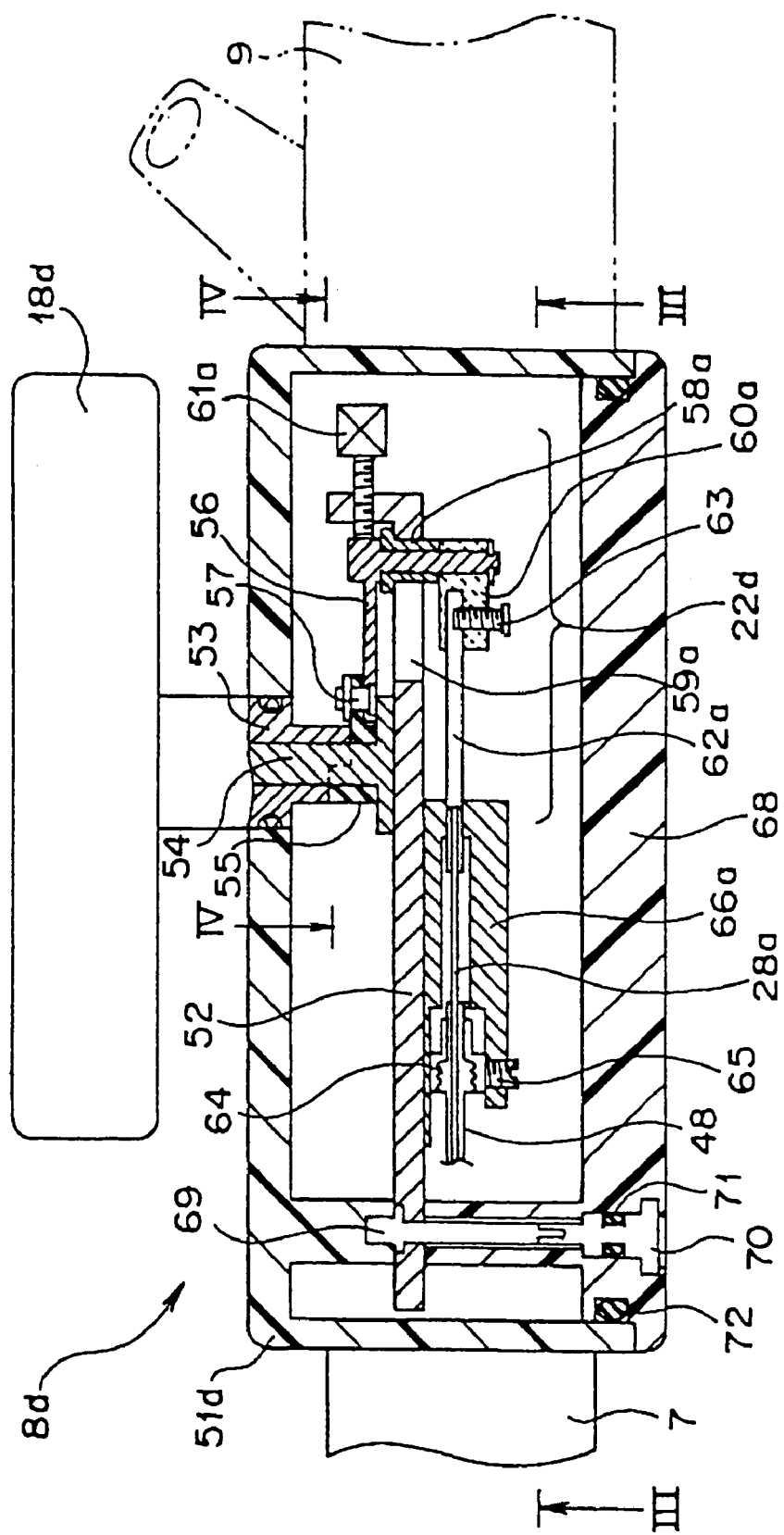
FIG. 14 is a cross-sectional view showing a main portion along the II-II direction shown in FIG. 13 according to the third embodiment of the present invention.
Figure 15:
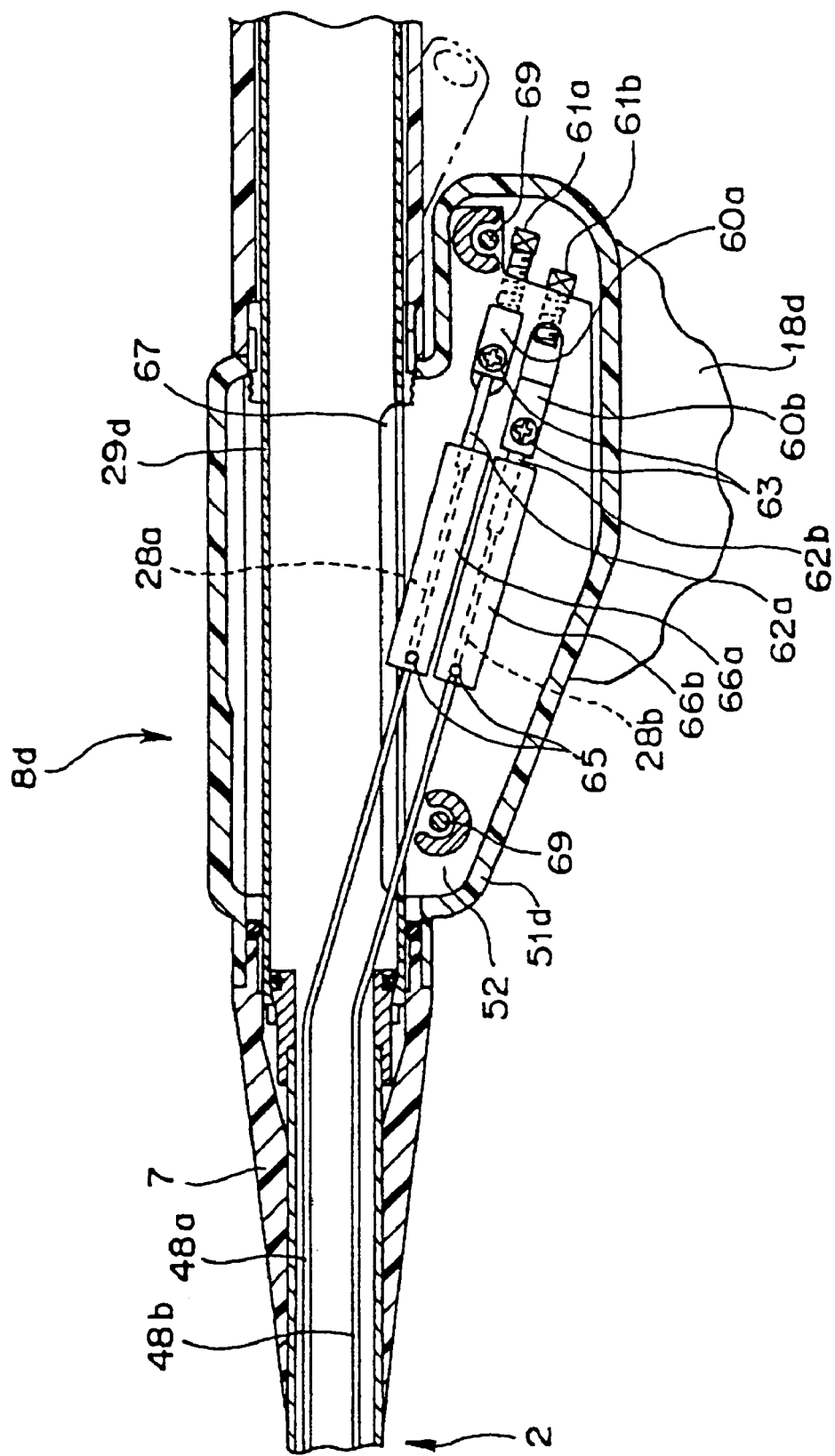
FIG. 15 is a cross-sectional view showing a main portion along the III-III direction shown in FIG. 14 according to the third embodiment of the present invention.
Figure 16:
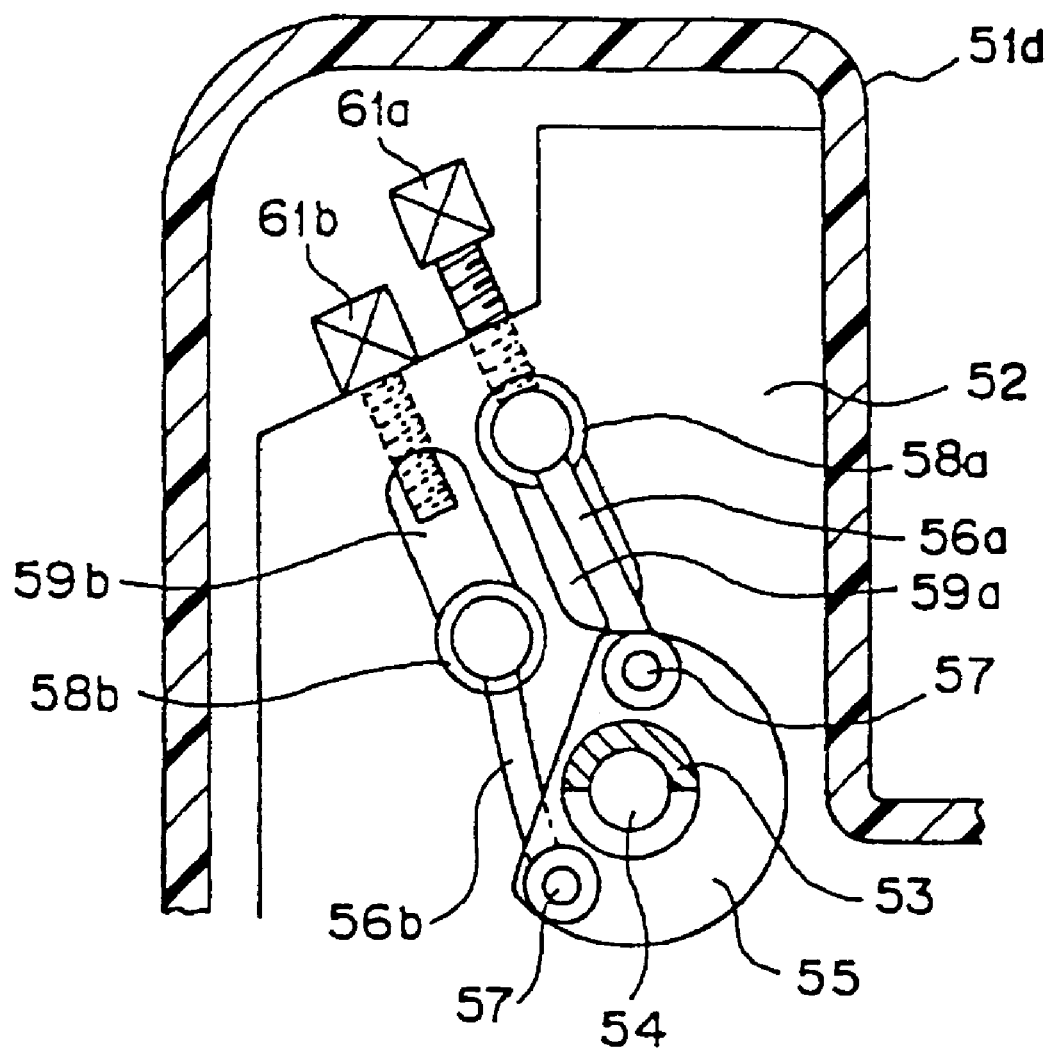
FIG. 16 is a cross-sectional view showing a main portion along the IV-IV direction shown in FIG. 14 according to the third embodiment of the present invention.
Figure 17:
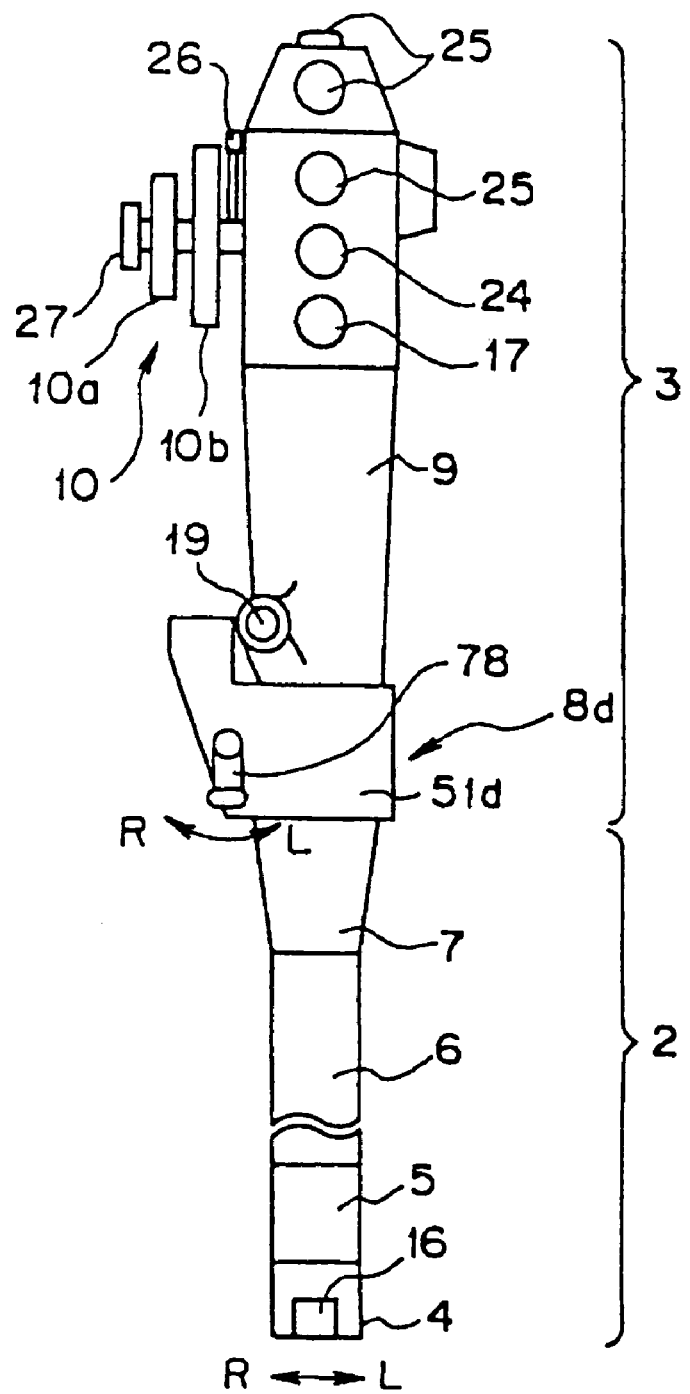
FIG. 17 is a front view showing an endoscope according to one modification of the third embodiment of the present invention.
Figure 18:
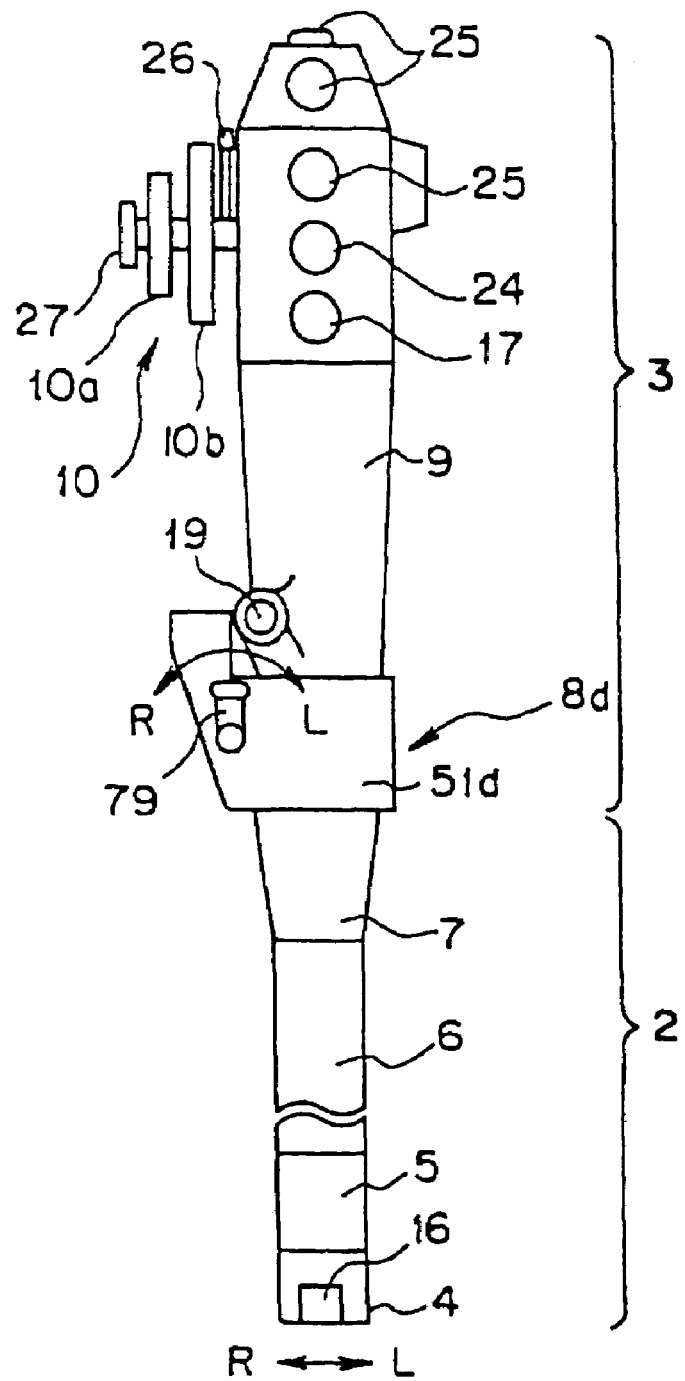
FIG. 18 is a front view showing an endoscope according to another modification of the third embodiment of the present invention.

Next, the third embodiment of the present invention will be described with reference to FIGS. 13 to 18. FIG. 13 is a front view showing the entire structure of an endoscope according to the third embodiment of the present invention. FIG. 14 is a cross-sectional view showing a main portion along the II-II direction shown in FIG. 13 according to the third embodiment of the present invention. FIG. 15 is a cross-sectional view showing a main portion along the III-III direction shown in FIG. 14 according to the third embodiment of the present invention. FIG. 16 is a cross-sectional view showing a main portion along the IV-IV direction shown in FIG. 14 according to the third embodiment of the present invention. FIG. 17 is a front view showing an endoscope according to one modification of the third embodiment of the present invention. FIG. 18 is a front view showing an endoscope according to another modification of the third embodiment of the present invention. According to the third embodiment, unlike the first embodiment, a controlling-base operating section 8d is formed by using a controlling-base operating knob 18d which rotates around the axis perpendicular to the longitudinal direction of the operating section 3, in place of the operating knob which rotates around the axis of the operating section 3. Others are the same as those according to the first embodiment, the same components are designated by the same reference numerals, and a description thereof is omitted.

Referring to FIG. 13, according to the third embodiment, a controlling-base operating frame 51d forming the controlling-base operating section 8d is arranged to the distal side of the operating section 3. The controlling-base operating knob 18d is arranged to the controlling-base operating section 8d. The controlling-base operating knob 18d as controlling-base operating means can freely be rotated in the right and left directions of the operator who grips the operating section 3 with the rotating axis perpendicular to the long axis of the operating section 3 as the center, on the front side of the arrangement of the air and fluid supply control button 17 and the suction control button 24.

Referring to FIGS. 14 to 16, the controlling-base operating frame 51d includes an operating main body substrate 52 which is tightened and fixed to an operating section main body 29d. A fixing shaft 54 projected to the controlling-base operating knob 18d is fixed to the operating section main body 29d. A cylindrical shaft 53 extended from the controlling-base operating knob 18d is pierced through the controlling-base operating frame 51d and is rotatably fit to the outer circumference of the fixing shaft 54. That is, the cylindrical shaft 53 of the controlling-base operating knob 18d is axially supported to the operating main body substrate 52 rotatably via the fixing shaft 54.

A rotating plate 55 is axially fixed to the fixing shaft 54. The rotating plate 55 is fit by a key into the cylindrical shaft 53. Thus, the rotating plate 55 is rotated integrally with the controlling-base operating knob 18d.

Referring to FIG. 16, pair of L-shaped rods 56a and 56b are axially fit to the rotating plate 55 via rotating pins 57. Free ends of the L-shaped rods 56a and 56b are vertically positioned to the operating main body substrate 52 side (refer to FIG. 14), and free ends of the L-shaped rods 56a and 56b are fit into a pair of guide grooves 59a and 59b opened to the operating main body substrate 52 via lubricating members 58a and 58b (refer to FIG. 16). Thus, the rotating operation of the rotating plate 55 which rotates according to the controlling-base operating knob 18d is converted into the straight movement on the free ends of the L-shaped rods 56a and 56b by the guide grooves 59a and 59b.

Referring to FIG. 14, the free ends of the L-shaped rods 56a and 56b are pierced through the guide grooves 59a and 59b and are exposed to the back side of the operating main body substrate 52. Brackets 60a and 60b are rotatably connected to the free ends of the L-shaped rods 56a and 56b.

Stoppers 61 corresponding to the L-shaped rods 56a and 56b are arranged to the operating main body substrate 52. The stoppers 61a and 61b comprise male screws which are screwed to the operating main body substrate 52, facing the free end side of the L-shaped rods 56a and 56b at the end sections of the stoppers 61a and 61b. The rotating range of the controlling-base operating knob 18d is variably set in accordance with the screwing amount to the operating main body substrate 52 of the stoppers 61a and 61b.

Referring to FIGS. 14 and 15, wire connecting members 62a and 62b forming a part of the operation transmitting member are detachably fixed, via screws 63, to the brackets 60a and 60b connected to the free ends of the L-shaped rods 56a and 56b.

In the controlling-base operating frame 51d, the proximal side of the tractional wire 28a connected to the right side of the therapeutic instrument controlling base 16 and the proximal side of the tractional wire 28b connected to the left side of the therapeutic instrument controlling base 16 are extended, and the proximal portions of the tractional wires 28a and 28b are connected and fixed to the wire connecting members 62a and 62b by the soldering or brazing.

With the above-mentioned structure, a controlling-base operating mechanism 22d controls such that the therapeutic instrument controlling base 16 moves in accordance with the rotating operation of the controlling-base operating knob 18d, and the controlling-base operating frame 51 includes the controlling-base operating mechanism 22d.

The tractional wires 28a and 28b are extended to the operating section 3 from the inserting portion 2 when the tractional wires 28a and 28b are inserted in operating wire guide tubes 48a and 48b. The proximal portions of the operating wire guide tubes 48a and 48b are screwed to a guide tube holding member 64 (refer to FIG. 14). Further, the guide tube holding member 64 is fixed and held to the distal side of the cylinders 66a and 66b via screws 65. The cylinders 66a and 66b comprise hollow members which are fixed to the operating main body substrate 52, and a connecting portion between the tractional wires 28a and 28b and the wire connecting members 62a and 62b is inserted into the cylinders 66a and 66b.

With the above-mentioned structure, when the controlling-base operating knob 18d is rotated in the right direction (clockwise direction in FIG. 13) in view of the operator who grips the operating section 3, the controlling-base operating mechanism 22d tracts the tractional wire 28a connected to the right side of the therapeutic instrument controlling base 16 to the operating section 3 side, and further presses out the tractional wire 28b connected to the left side of the therapeutic instrument controlling base 16 to the inserting portion 2 side and the therapeutic instrument controlling base 16 is moved in the right direction. On the contrary, when the controlling-base operating knob 18d is rotated in the left direction (anticlockwise direction in FIG. 13), the controlling-base operating mechanism 22d presses out the tractional wire 28a connected to the right side of the therapeutic instrument controlling base 16 to the inserting portion 2 side and further tracts the tractional wire 28b connected to the left side of the therapeutic instrument controlling base 16 to the operating section 3 side. Thus, the therapeutic instrument controlling base 16 is moved in the left direction. That is, the controlling-base operating mechanism 22d controls such that the therapeutic instrument controlling base 16 moves in the direction matching the operating direction of the controlling-base operating knob 18d.

As mentioned above, controlling-base operating mechanism 22d is formed by arranging, on the operating main body substrate 52, the proximal sides of the operating wire guide tubes 48a and 48b and the proximal sides of the tractional wires 28a and 28b. Further, the controlling-base operating mechanism 22d is accommodated in the controlling-base operating frame 51 which is offset to the outside of an operating section main body 29d.

Therefore, in order to construct the controlling-base operating mechanism 22d in the controlling-base operating frame 51, notch windows 67 for notching the operating wire guide tubes 48a and 48b and the like therein are opened to the operating section main body 29d.

Referring to FIG. 14, the controlling-base operating frame 51 is closed by a cover 68. Specifically, the cover 68 is tightened and fixed, by a support fixing screw 70, to supports 69 implanted to the operating main body substrate 52 of the controlling-base operating frame 51. In this case, a watertight mechanism portion 71 is arranged between the cover 68 and the support fixing screws 70. A watertight member 72 is arranged between the controlling-base operating frame 51 and the cover 68. Thus, the controlling-base operating frame 51 is sealed.

According to the third embodiment, the operating direction of the controlling-base operating knob 18d matches the swinging direction of the therapeutic instrument controlling base 16 and consequently, the same advantages as those according to the first embodiment are obtained.

In this case, the controlling-base operating knob 18d may be arranged to the back surface of the controlling-base operating frame 51 in view of the operator who grips the operating section 3.

According to the third embodiment, referring to FIG. 17, a controlling-base operating lever 78 directed, at the free end thereof, to the distal side of the operating section 3 may be applied as the controlling-base operating means, in place of the controlling-base operating knob 18d. Further, referring to FIG. 18, a controlling-base operating lever 79 directed, at the free end thereof, to the proximal side may be applied as the controlling-base operating means, in place of the controlling-base operating knob 18d. In this case, the connecting state of the wire connecting members 62a and 62b to the brackets 60a and 60b are properly switched and thus the operating direction of the controlling-base operating lever 78 (or 79) matches the swinging direction of the therapeutic instrument controlling base 16.

According to the first to third embodiment, the electric endoscope has been described with the solid-state image pick-up element for obtaining the observed image of the object, as one example of the endoscopes according to the present invention. However, the present invention is not limited to this. For example, the present invention can be applied to a fiber scope using an optical fiber as means for transmitting the observed image. In this case, when the operator who grips the operating section operates the controlling-base operating means in the right direction, the therapeutic instrument controlling base is moved in the right direction of the image which is observed by the operator. When the controlling-base operating means is operated in the left direction, the therapeutic instrument controlling base is moved in the left direction of the image which is observed by the operator.

The controlling-base operating mechanism for controlling such that the therapeutic instrument controlling base moves in the right and left directions of the observed image is not limited to the mechanical device which is described according to the first to third embodiments. The controlling-base operating mechanism may electrically operate the therapeutic instrument controlling base in accordance with the operation input to the controlling-base operating means of the operator. In this case, the direction for inputting the operation of the operator matches the moving direction of the therapeutic instrument controlling base.

What is claimed is:

1. An endoscope comprising:
    an elongated inserting portion which is inserted in an object;
    observing means which is arranged at an end portion of the inserting portion;
    a therapeutic instrument controlling base which is pivotally supported to a distal portion of the inserting portion so as to be able to control a therapeutic instrument in the right and left directions of an observed image obtained by the observing means, and which has a contact portion that comes in contact with a therapeutic instrument projected from an opening of a channel for inserting the therapeutic instrument at the distal portion of the inserting portion as the therapeutic instrument is controlled;
    controlling-base operating means which is arranged on a distal side in an insertion direction of a therapeutic instrument inserting port into which the therapeutic instrument is inserted and directly adjacent to the therapeutic instrument inserting point, in an operating section arranged at a proximal side portion of the inserting portion and which can be operated in the right and left directions of an operator who grips the operating section; and
    a controlling-base operating mechanism which controls such that the therapeutic instrument controlling base moves in the right direction of the observed image according to the operation of the controlling-base operating means in the right direction thereof by the operator and controls such that the therapeutic instrument controlling base moves in the left direction of the observed image according to the operation of the controlling-base operating means in the left direction thereof, the right and left controlling direction of the therapeutic instrument controlling base and the right and left operating direction of the controlling-base operating means being in parallel to each other when the inserting portion is substantially straight.

2. An endoscope according to claim 1, wherein the right and left directions of the therapeutic instrument controlling base match the right and left directions of the observed image displayed on a monitor.

3. An endoscope according to claim 1, wherein the inserting portion includes a bending portion which bends the end section of the inserting portion in at least up and down directions.

4. An endoscope according to claim 3, wherein the up and down directions of the end section match the up and down directions of the observed image displayed on a monitor.

5. An endoscope according to claim 1, wherein the controlling-base operating means includes a controlling-base operating knob which is rotated in the circumferential direction of the operating section with respect to long axis of the operating section as the rotating axis along the distal side from the proximal side of the operating section, and the controlling-base operating mechanism controls such that the therapeutic instrument controlling base moves in the fight direction of the observed image according to the rotating operation in the right direction of the controlling-base operating knob by the operator who grips the operating section, and controls such that the therapeutic instrument controlling base moves in the left direction of the observed image according to the rotating operation in the left direction of the controlling-base operating knob.

6. An endoscope according to claim 5, wherein the controlling-base operating knob is arranged to the distal side of the operating section.

7. An endoscope according to claim 5, wherein the controlling-base operating mechanism comprises:
a cam ring which rotates with the controlling-base operating knob;
a pair of sliding members which advance and return in the opposite directions each other along the direction of the rotating axis of the cam ring by the rotation of the cam ring, and
the therapeutic instrument controlling base is moved according to the advance and return movement of the pair of the sliding members.

8. An endoscope according to claim 7, wherein the controlling-base operating mechanism operates the therapeutic instrument controlling base via an operation transmitting member.

9. An endoscope according to claim 8, wherein the operation transmitting member comprises a tractional wire which connects the right side and left side of the therapeutic instrument controlling base to the sliding members.

10. An endoscope according to claim 1, wherein the controlling-base operating means is an operating slider which can be moved in the right and left directions of the operator who grips the operating section, and the controlling-base operating mechanism controls such that the therapeutic instrument controlling base moves in the right direction of the observed image according to the operation of the operating slider in the right direction of the operator who grips the operating section, and controls such that the therapeutic instrument controlling base moves in the left direction of the observed image according to the operation of the operating slider in the left direction.

11. An endoscope according to claim 10, wherein the controlling-base operating mechanism comprises:
a cam ring which rotates according to the moving operation of the operating slider; and
a pair of sliding members which advance and return in the opposite direction each other along the direction of the rotating axis of the cam ring by the rotation of the cam ring, and
the therapeutic instrument controlling base moves according to the advance and return of the sliding members.

12. An endoscope according to claim 11, wherein the controlling-base operating mechanism controls such that the therapeutic instrument controlling base moves via an operation transmitting member.

13. An endoscope according to claim 12, wherein the operation transmitting member comprises a tractional wire which connects the right side and left side of the therapeutic instrument controlling base and the sliding members.

14. An endoscope according to claim 1, wherein the controlling-base operating means includes a controlling-base operating knob which can freely be rotated in the right and left directions of the operator who grips the operating section with the rotating axis, as center, perpendicular to the long axis of the operating section along the distal side from the proximal side of the operating section, and the controlling-base operating mechanism controls such that the therapeutic instrument controlling base moves in the right direction according to the rotating operation of the controlling-base operating knob in the right direction by the operator who grips the operating section, and controls such that the therapeutic instrument controlling base moves in the left direction according to the rotating operation of the controlling-base operating knob in the left direction.

15. An endoscope according to claim 14, wherein the controlling-base operating mechanism comprises:
a rotating plate which rotates according to the controlling-base operating knob; and
a pair of guide grooves which convert the movement on the free end sides of a pair of L-shaped rods axially-fixed to the rotating plate into the straight movement in the opposite direction each other, and
the therapeutic instrument controlling base is moved according to the straight movement of the L-shaped rods.

16. An endoscope according to claim 1, wherein the controlling-base operating means includes a controlling-base operating lever which can freely be rotated in the right and left directions of the operator who grips the operating section with the rotating axis, as center, perpendicular to the long axis of the operating section along the distal side from the proximal side of the operating section, and the controlling-base operating mechanism controls such that the therapeutic instrument controlling base moves in the right direction according to the rotating operation of the controlling-base operating lever in the right direction of the operator who grips the operating section, and controls such that the therapeutic instrument controlling base moves in the left direction according to the rotating operation of the controlling-base operating lever in the left direction.

17. An endoscope according to claim 16, wherein the controlling-base operating mechanism comprises:
   a rotating plate which rotates according to the controlling-base operating lever; and
   a pair of guide grooves which convert the movement of the free end sides of a pair of L-shaped rods axially fixed to the rotating plate into the straight movement in the opposite direction each other, and
   the therapeutic instrument controlling base is moved according to the straight movement of the L-shaped rods.

18. An endoscope comprising:
   an elongated inserting portion which is inserted in an object;
   observing means which is arranged at an end portion of the inserting portion;
   a therapeutic instrument controlling base which is pivotally supported to a distal portion of the inserting portion so as to be able to control a therapeutic instrument in the right and left directions of an observed image obtained by the observing means, and which has a contact portion that comes in contact with a therapeutic instrument projected from an opening of a channel for inserting the therapeutic instrument at the distal portion of the inserting portion as the therapeutic instrument is controlled;
   controlling-base operating means which is arranged on a distal side in an insertion direction of a therapeutic instrument inserting port into which the therapeutic instrument is inserted and directly adjacent to the therapeutic instrument inserting point, in an operating section arranged at a proximal side portion of the inserting portion and which can be operated in the right and left directions of an operator who grips the operating section, the controlling-base operating means disposed at the proximal side portion of the inserting portion to rotate coaxially with a longitudinal axis of the inserting portion; and
   a controlling-base operating mechanism which controls such that the therapeutic instrument controlling base moves in the right direction of the observed image according to the operation of the controlling-base operating means in the right direction thereof by the operator and controls such that the therapeutic instrument controlling base moves in the left direction of the observed image according to the operation of the controlling-base operating means in the left direction thereof.

* * * * *